United States Patent
Chang et al.

(10) Patent No.: US 7,033,777 B2
(45) Date of Patent: Apr. 25, 2006

(54) METHOD FOR DETECTING COCKROACH ALLERGENS AND DETERMINING TOTAL ALLERGEN LEVEL

(75) Inventors: Frank N. Chang, Dresher, PA (US); Phu T. Duong, Malvern, PA (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 271 days.

(21) Appl. No.: 10/392,239

(22) Filed: Mar. 19, 2003

(65) Prior Publication Data

US 2003/0180826 A1 Sep. 25, 2003

Related U.S. Application Data

(60) Provisional application No. 60/367,063, filed on Mar. 22, 2002.

(51) Int. Cl.
*C12Q 1/00* (2006.01)
*C12Q 1/34* (2006.01)
*C12Q 1/37* (2006.01)
*A61K 38/47* (2006.01)

(52) U.S. Cl. .............................. 435/18; 435/4; 435/23; 424/94.61

(58) Field of Classification Search .................... 435/4, 435/18, 23; 424/94.61
See application file for complete search history.

(56) References Cited

U.S. PATENT DOCUMENTS

| | | | |
|---|---|---|---|
| 3,654,090 A | 4/1972 | Wilhelmus et al. | |
| 4,016,043 A | 4/1977 | Schuurs et al. | |
| 4,250,394 A | 2/1981 | O'Connor | |
| 4,528,267 A | 7/1985 | Calenoff et al. | |
| 4,716,120 A | 12/1987 | Tsay et al. | |
| 4,845,027 A | 7/1989 | Calenoff et al. | |
| 4,849,337 A | 7/1989 | Calenoff et al. | |
| 5,206,143 A | 4/1993 | Horan et al. | |
| 5,480,775 A | 1/1996 | Ito et al. | |
| 5,486,452 A | 1/1996 | Gordon et al. | |
| 5,679,535 A | 10/1997 | Joyce et al. | |
| 5,869,288 A | 2/1999 | Chapman et al. | |
| 5,981,287 A | 11/1999 | Sinclair et al. | |
| 6,060,598 A | 5/2000 | Devlin et al. | |
| 6,087,947 A | 7/2000 | Hamburger et al. | |
| 6,231,519 B1 | 5/2001 | Blants et al. | |

OTHER PUBLICATIONS

Y. Ren, K. E. Wee, and F. N. Chang, Deficiency of Current Methods in Assaying Endochitinase Activity, Biochemical and Biophysical Research Communications 268 ,pp. 302-305, (2000).

D. L. Rosenstreich, M.D., P. Eggleston, M.D., M. Kattan, M.D., D. Baker, M.D., M.P.H., R. G. Slavin, M.D., P. Gergen, M.D., H. Mitchell, PH. D., K. Mcniff-Mortimer, M.P.H., H. Lynn, PH.D., D. Ownby, M.D. and F. Malveaux, M.D., PH.D., The Role Of Cockroach Allergy And Exposure To Cockroach Allergen In Causing Morbidity Among Inner-City Children With Asthma; The New England Journal of Medicine, vol. 336, pp. 1356-1363, May 8, 1997, No. 19.

K. Arruda, L. D. Vailes, B. J. Mann, J Shannon, J. W. Fox, T. S. Vedvick, M. L. Hayden, and Martin D. Chapman, Molecular Cloning of a Major Cockroach (*Battella germanica*) Allergen, Bla g 2, The Journal of Biological Chemistry, vol. 270, No. 33, Issue of Aug. 18, pp. 19563-19568, 1995.

L. K. Arruda, L. D. Vailes, M. L. Hayden, D. C. Benjamin, and M. D. Chapman, Cloning of Cockroach Allergen, Bla g 4, Identifies Ligand Binding Proteins (or Calycins) as a Cause of IgE Antibody Responses, The Journal of Biological Chemistry, vol. 270, No. 52, Issue of Dec. 29, pp. 31196-31201, 1995.

(Continued)

*Primary Examiner*—Ruth A. Davis
(74) *Attorney, Agent, or Firm*—RatnerPrestia

(57) ABSTRACT

The present invention is directed to a method and a test kit for detecting cockroach allergens and/or determining the total allergen level. A sample from an environment in which cockroaches are present or are suspected to be present is provided. The sample and a substrate composition comprising a chitinase substrate are then contacted. The presence of cockroach allergens can be determined by observing or detecting the magnitude of a measurable change of a property of the substrate composition following the contact between the sample and the substrate composition wherein the magnitude of the measurable change of a property of the substrate composition is proportional to the total allergen level. The total allergen level can be determined by measuring the magnitude of the measurable change of a property of the substrate composition, or by comparing the magnitude with a reference standard.

22 Claims, 3 Drawing Sheets

OTHER PUBLICATIONS

L. K. Arrude, L. D. Vailes, T. A. E. Platts-Mills, M. L. Hayden, and M. D. Chapman, Induction of IgE Antibody Reponses by Glutathione S-Transferase from the German Cockroach (*Blattella germanica*), The Journal of Biological Chemistry, vol. 272, No. 33., Issue of Aug. 15, pp. 20907-20912, 1997.

R. G. Hamilton, Laboratory Analyses In The Diagnosis Of Human Allergic Disease, A Companion to Methods in Enzymology 13, 25 25-31 (1997).

Detection of Endochitinase and Exochitinase Activities

Detection Limit of 4-methylumbelliferone (top panel)

(bottom panel)

METHOD FOR DETECTING COCKROACH ALLERGENS AND DETERMINING TOTAL ALLERGEN LEVEL

CROSS-REFERENCE TO RELATED APPLICATIONS

This application claims the benefit of the priority date of Provisional U.S. Patent Application Ser. No. 60/367,063, filed Mar. 22, 2002 for the subject matter disclosed therein.

FIELD OF THE INVENTION

The present invention relates to allergens. More specifically, it relates to a method and a test kit for detecting cockroach allergens and/or determining the total allergen level.

BACKGROUND OF THE INVENTION

About 17.3 million Americans suffer from asthma, which is a chronic inflammatory disorder of the airways. In susceptible individuals, this inflammation causes recurrent episodes of coughing, wheezing, chest tightness and difficult breathing. Inflammation makes the airways sensitive to indoor allergens such as those derived from cockroaches, dust mites and animal dander. Asthma is also the most common chronic childhood illness, particularly in inner-city homes, and is the leading cause of children's emergency room use, hospital admission and school absence. Chronic asthma in children is highly associated with chronic respiratory disease in adulthood and has a huge health, economical and societal impact.

An extensive study was carried out by the National Cooperative Inner-City Asthma Groups, evaluating over 1500 children from eight major cities in the United States for the contribution of various indoor allergens to asthma. It was reported that of the three major indoor allergens, cockroach allergens, dust mites and animal dander, only allergens from German cockroaches showed a positive correlation with the incidence of asthma. (See Rosenstreich et al., New England J. of Med., 336 (19): 1356–1363, 1997).

Cockroach allergens are protein molecules found in their fecal pellets, dead body parts, shed cuticles and egg cases, and secretions that, when aerosolized and inhaled, trigger IgE-mediated allergic reactions to produce asthma and/or related respiratory conditions or diseases. Fumigating homes with pesticides or using baits containing toxic chemicals may initially have appeared to reduce the number of cockroaches due to the return of poisoned cockroaches to their nesting places, usually cracks and crevices, to die. But in reality, this did not reduce the indoor allergen level because the cockroaches' dead body parts, fecal pellets, and associated allergens still remained in treated homes and later became airborne and circulated in the homes. Aside from leaving toxic residues in the treated homes, the use of chemical insecticides may actually increase the allergen burden by speeding up the decaying and aerosolization processes. Cockroach allergens were also reported to be exceptionally stable and remained active for at least five years after they were produced.

Preventing the development of asthma is a major goal of current research. To achieve this goal, both the cockroaches and their associated allergens need to be removed. Efficient attractant and pheromone-based sticky traps are commercially available for catching the cockroaches. In order to eliminate the allergens produced by cockroaches, one has to know not only the exact locations of the contaminated areas but also the severity of the contamination. Currently available allergen determination procedures have failed to address these issues.

Current procedures for allergen level determination involves collecting dust samples from small arbitrary chosen areas (usually 1 m$^2$), typically from the kitchen and/or living room, vacuuming the areas for about two minutes to collect the dust samples for analysis, then sending the dust samples to a qualified laboratory for testing as further described below. (See R. G. Hamilton, Methods: A companion to Methods in Enzymology, 13, 25–32, 1997) This procedure is based on the assumptions that aerosolized allergens will settle down as dust and the cockroaches will also deposit allergens in these areas. As indicated earlier, the source of the cockroach allergens comes from their decayed fecal pellets, decayed dried body parts, decayed shed cuticles and egg cases, and secretions which are usually found in their nesting places, such as cracks and crevices, and these are not easily accessible for detection and cleaning. Thus, currently used sampling and testing methods are not suitable for finding the locations of the cockroach nesting places and identifying other areas of intense infestation.

Aqueous extracts of ground cockroach whole body have been used for allergy testing. At least six different protein allergens from German cockroach (*Blatella gemanica*) whole body have either been purified or cloned. (See Arruda et al., The J. of Biol. Chem., 270 (33), 19563–19568, 1995; 270 (52), 31196–31201, 1995; and 272 (33), 20907–20912, 1997; U.S. Pat. No. 5,869,288) They are called Bla g 1 through Bla g 6, according to the order of their discovery. Currently, only indirect methods utilizing tagged secondary antibodies (for example, Enzyme-Linked Immunosorbent Assay (ELISA)) are used to quantify one or two cockroach allergens (Bla g 1 and/or Bla g 2). Furthermore, because there are so many allergens produced by cockroaches, the amount of Bla g 1 and/or Bla g 2 may not be proportional to the total allergen level at all, and the distribution of Bla g 1 and Bla g 2 among the various sources of allergens is simply not known and is highly variable from site to site. Additionally, these methods are very expensive because they require specific monoclonal antibodies against either Bla g 1 or Bla g 2 and can only be performed in a limited number of laboratories. These methods are also very time-consuming, usually requiring 2 days to complete the allergen level determination. Therefore, it is highly impractical for homeowners, pest control operators, healthcare professionals, small business owners (such as restaurant owners), etc. to collect the dust samples from arbitrarily chosen areas, mail them to the laboratory, and wait one or two weeks for the results to come back.

Cockroach allergen studies reported so far used mainly extracts from ground live cockroaches (the so-called whole body extract). Applicants have found that indoor cockroach allergens are not present in nor derived directly from live cockroaches per se as commonly perceived, but rather from their decayed fecal pellets, decayed dried dead body parts, decayed shed cuticles, and secretions (collectively called the "frass"). As the decay process occurs, the breakdown of the frass components produces the protein allergens discussed above which, when aerosolized and circulating in an indoor environment, enter the respiratory system and trigger the IgE-mediated immune response that leads to allergy and/or asthma.

Further, applicants have unexpectedly discovered that two very stable enzymes, endochitinase and exochitinase (each referred to herein as a "chitinase"), are associated with the cockroach allergens collected from both the dust samples and all cockroach frass components (decayed fecal pellets, decayed dried body parts, egg cases and cuticles, and secretions). As will be illustrated in the following Examples, the level of either one or both of these two enzymes has been found to be proportional to the total cockroach allergen level present in either the frass or the dust samples, thus making chitinases ideal markers for measurement of the total indoor cockroach allergen level in these samples. Thus, the determination of total allergen level may be made by any technique suitable for chitinase detection.

These markers are enzymes or enzyme complexes involved in the hydrolysis of the chitin molecule. Chitin, an insoluble linear $\beta$-1, 4-linked polymer of N-acetyl-$\beta$-D-glucosamine (NAG), is present in all arthropods, yeast, most fungi and some stages of nematodes. Insect chitins are usually hydrolyzed by a combination of endochitinase, which randomly cleaves the chitin molecule internally to generate predominately NAG dimers (together with some trimers and tetramers) and exochitinase (also referred to as N-acetyl-$\beta$-glucosaminidase) to generate NAG monomers. To speed up the degradation of chitin, some organisms may additionally contain a different form of endochitinase called chitobiosidase which generates exclusively NAG dimers.

Applicants have discovered that when one or both of these chitinase enzymes are present in a sample, as hereinafter defined, from an environment or site in which cockroaches are present or are believed to be present, the presence of cockroach allergens in such samples and/or the level thereof, may be immediately measured by contacting the sample with a substrate composition comprising a chitinase substrate that undergoes a measurable change of a property, such as a change in color or fluorescence, when reacted with a chitinase. The change of the property is due to a physical transformation or chemical reaction, such as hydrolysis, between the chitinase in the sample and the chitinase substrate. The magnitude of the measurable change of the property can be immediately measured, either visually or with instruments such as a fluorometer, as an indirect measurement of the total cockroach allergen level in the samples. This method for determining the total cockroach allergen levels in environments in which cockroaches may be present, as described below, can be practiced not only directly on-site but also rapidly, inexpensively, and without the cost or delays inherent in currently available test procedures, for example, the ELISA test procedure. Thus, the method of the present invention relies on the newly discovered correlation between the stable chitinase enzyme level and the total allergen level, and is thus adapted to any technique suitable for chitinase detection, while the methods of the prior art require the difficult direct determination of only one or two specific allergens from live cockroaches. The present invention not only addresses the deficiencies of the current allergen detection methods but also provides a simple alternative method that can be easily practiced on-site (for example by homeowners, healthcare professionals, pest control operators, etc.) without the cost or delays inherent in currently available test procedures, for example, the ELISA test procedure.

SUMMARY OF THE INVENTION

The present invention is directed to a method and a test kit for detecting cockroach allergens and/or determining the total allergen level in environments in which cockroaches are present or are suspected to be present, and/or for removal of the causative agents, thereby decreasing the incidence of allergic reactions or asthma.

In accordance with the test method of the invention, a sample, as defined below, is provided from an environment or at a site at which cockroaches are known or believed to be present. The sample is then contacted with a substrate composition comprising a chitinase substrate for a period of time sufficient to cause a measurable change in a property resulting from reaction of any chitinase present in the sample with the chitinase substrate. Then, the presence of cockroach allergens and/or total allergen level in the sample is determined or assessed by detecting, observing and/or measuring the magnitude of the measurable change. The measurable change in property may occur instantly upon contact of the sample with the substrate composition or may require a brief period of contact to permit reaction to proceed between the sample and substrate composition. The measurable change of a property may comprise the liberation of a color, change of color or intensity of color, or the liberation of fluorescence, for example. The magnitude of the change produced is a measure of the chitinase level in the sample and is proportional to the total allergen level thereof.

According to one aspect of the method, the magnitude of the measurable change of a property following contact between the sample and the substrate composition may be visually observed or is detected, for example with a fluorescence detector. Alternatively or in addition, the magnitude of the measurable change may be measured or compared with a reference standard having correlation between the magnitude of measurable change and the total allergen level.

In accordance with a further aspect of the invention, there is provided a method for decreasing or eliminating the incidence of allergic reactions or asthma. This method comprises the allergen detection and/or determination procedures, in accordance with the method described above, then removing the materials containing the allergens, and/or the allergens themselves, from the area where unacceptable allergen levels are detected.

In the embodiments described herein, the method may further comprise sieving the sample prior to contacting the sample and the substrate composition. In addition, the step of contacting the sample and the substrate composition may include extracting the sample with a buffer solution to produce a liquid extract, solution or suspension comprising the chitinases, contacting the resulting liquid with the substrate composition or a solution of the chitinase substrate, then terminating the reaction.

In accordance with the test kit of the invention, the test kit comprises a substrate composition comprising a chitinase substrate and a reference standard. The substrate composition is as described in connection with the method aspect of this invention. The reference standard provides a correlation between the magnitude of measurable change of a property of the substrate composition and the total allergen level in the sample. The test kit may also comprise means for sieving a sample to separate out debris and undegraded body components, such as intact body parts, prior to testing of the sample. The test kit may also include means for measuring and delivering a measured amount of sample and delivering a measured amount of substrate composition for contact with the sample.

It is to be understood that both the foregoing general description and the following detailed description are exemplary, but not restrictive, of the invention.

DETAILED DESCRIPTION OF THE PRESENT INVENTION

Figure 1:
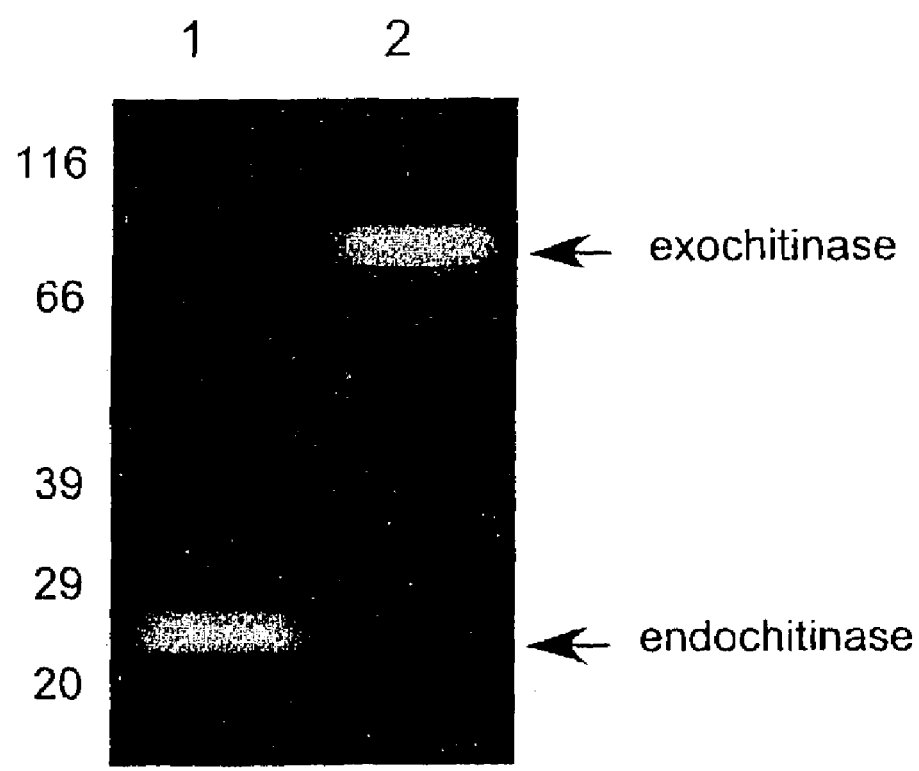
FIG. 1 is an SDS-PAGE gel showing the presence of endochitinase activity and exochitinase activity of frass extracts from German cockroaches in EXAMPLE 1.
Figure 2:
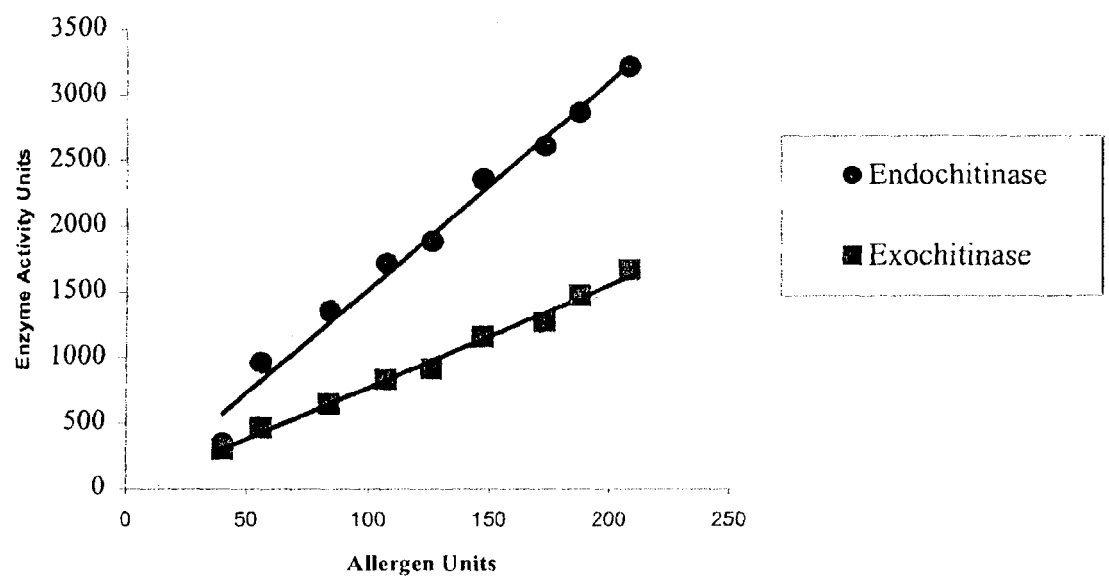
FIG. 2 is a graph showing the results of endochitinase activity and exochitinase activity in comparison to the total allergen level for different dust and frass samples.
Figure 3:
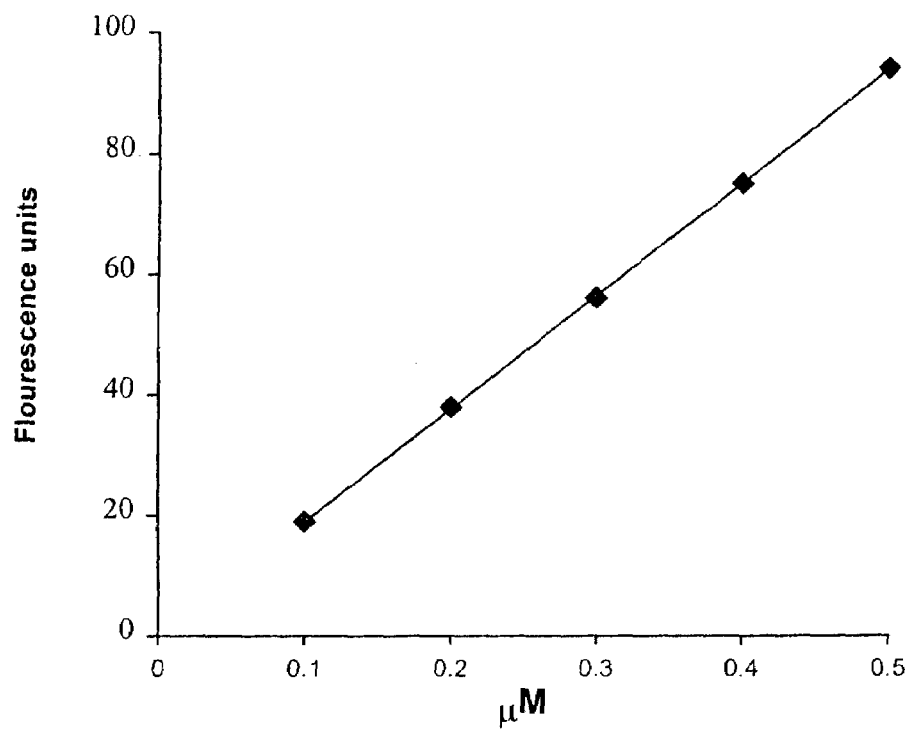
FIG. 3 is a graph (top panel) and a Whatman paper (bottom panel) showing the limit of detection of 4-methylumbelliferone (4MU).
Figure 3:
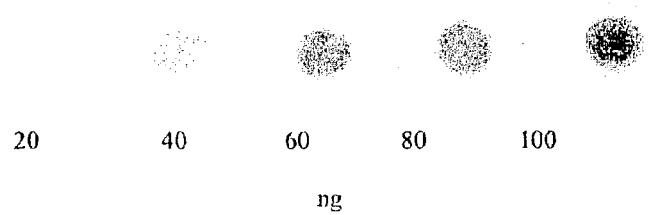

Referring to FIGS. 1–3, the present invention is directed to a method and a test kit for detecting of allergens and/or determining the total allergen level in environments in which cockroaches are known or believed to be present, and/or for removal of the causative agents, thereby decreasing the incidence of allergic reactions or asthma.

In accordance with the present invention, the following terms have the meanings indicated below:

The terms "sample" or "samples" are used to refer to a material collected from or present in an environment at or near a site where cockroaches are known or believed to be present, the allergen content of which is unknown and is to be determined in accordance with the invention. In general it may be a quantifiable or weighable sample in solid form, for example dust which has settled in proximity to the site or dust collected proximate to the site. Preferably the sample materials is provided or taken from a location in or near cockroach nesting-places, such as cracks and crevices. Also it may be in the form of a liquid solution of the solid form, for example an extract of dust or degraded cockroach body parts found at the site.

The term "chitinase substrate" is used to refer to any chemical, biochemical or biological species that complexes with, reacts with, or otherwise interacts with a chitinase enzyme such as endochitinase or exochitinase to produce a measurable change in a property such as a change in color, intensity of color or liberation of fluorescence.

The term "substrate composition" is used to refer to any macroscopic substance, including but not limited to solutions or other liquids and impregnated porous materials or other solids which contain chitinase substrate.

The terms "color" or "fluorescence" are used only to provide examples of the measurable change in a property resulting from contact and interaction of the substrate composition with a sample containing chitinase enzyme. It will be understood by those skilled in the art these terms are exemplary of the types of changes that may be applicable to the present invention, and are not used to limit the measurable change in a property or to limit the types of changes embraced within the broad scope of the present invention. Similarly, the terms "chromogenicsubstrate" or "fluorogenic substrate" are used only to provide examples of the chitinase substrate that may be applicable to the present invention, and are not used to limit the chitinase substrate to only these two examples. The terms "fluorogenic substrate" and "fluorophore" may be used interchangeably to describe a chitinase substrate that is hydrolyzed by or otherwise reacted with endochitinase and/or exochitinase upon contact therewith, producing a complex, product or other derivative thereof which liberates fluorescence upon excitation by a suitable light source when sufficient endochitinase and/or exochitinase is present in the sample. The terms "chromogenic substrate" and "chromophore" may be used interchangeably to describe a chitinase substrate that is hydrolyzed by or otherwise complexed or reacted with endochitinase and/or exochitinase upon contact therewith, producing a product or colored derivative thereof which liberates color when sufficient endochitinase and/or exochitinase is present in the sample.

The chitinase substrates are commercially available and fall into two major categories, namely absorbance-based and fluorescence-based. For both absorbance-based and fluorescence-based assays, it is suitable that the chitinase substrates used in the method are initially either substantially colorless or substantially non-fluorescent, respectively. The fluorescence-based measurements can be several orders of magnitude more sensitive than the absorbance-based ones. If a substrate is used which has a low level of color or fluorescence, that level can be subtracted from the final color or fluorescence to more accurately measure the color or fluorescence liberated by the activity of the chitinase on the chitinase substrate, as shown in the examples.

In accordance with the method of the invention, a sample is provided in situ, for example as settled dust, or is taken from an environment or site, such as a room or kitchen floor in an apartment or house, including, for example, cockroach nesting-places such as cracks and crevices in such locations, in which cockroaches are known or believed to be present. The sample may comprise various components, such as dust and decayed and undecayed cockroach body parts and 'frass' as indicated above. When cockroaches are pesent at or near sampling site, the sample will include various levels of chitinase enzymes including endochitinase, exochitinase or a combination thereof which are tested for in accordance with the present invention.

The samples may be used as such, or they may be sieved prior to contact with the substrate composition to remove the larger particles, for example those body parts of dead cockroaches which are still intact and undegraded and other debris, thereafter utilizing the sieved product resulting after removal of such undegraded body parts.

Depending on the location from which the samples are taken, and in particular the location having high concentrations of cockroach allergens (such as nesting sites of cockroaches), the allergen level can simply be determined by using the method described in the invention. It may also be desirable to take and test multiple samples from various locations at the site. The direct allergen detection method described herein may enable pest control operators and the like to locate and to determine the areas of greatest allergen contamination and to eradicate cockroach nesting sites which are not apparent from visual inspection of the site.

Another aspect of the invention is to use the allergen detection method described here as a monitoring tool during and after the allergen removal process and to ensure that the treated sites are free of allergens. Thus, the method of the invention is also a monitoring tool crucial to the reduction of the incidence of asthma.

For purposes of testing in accordance with the present invention, very small samples may be utilized. A typical sample for testing, for example may suitably be in the range of about 0.01 gram to about 5 grams, although larger samples may be employed if desired.

In accordance with the method of the invention, each sample is then contacted with a substrate composition comprising a chitinase substrate, such as a fluorogenic substrate, a chromogenic substrate or a mixture thereof, for a period of time, preferably a brief period, and under conditions sufficient to permit the chitinase of the sample to react with the chitinase substrate of the substrate composition to cause a measurable change in a property, such as an intensity of color or fluorescence, of the resulting reaction product.

In general either the sample or the substrate composition must be in a liquid form to enable the reaction to proceed promptly and efficiently between the chitinase of the sample and chitinase substrate of the substrate composition. Thus, for example if a sample of dust is being tested in-situ, or is collected for testing without modification, the substrate composition must be in the form of a liquid, which may be prepared, for example, in a suitable buffer solution as described in the examples, and dropped in or blended with the solid sample. Conversely, if the sample is extracted or incorporated into a liquid vehicle such as a buffer solution, the substrate composition may be in the form of a liquid or a solid or may be incorporated into a supporting structure such as a filter or other suitable membrane.

For purposes of testing in accordance with the present invention, the amount of chitinase substrate that is used generally will depend on the size of the sample that is utilized or tested. A typical concentration of chromogenic or fluorogenic substrate in a liquid substrate composition that is used in the testing method is, for example, in the range of about 0.1 µM to about 5.0 mM, although larger or smaller amounts may be employed if desired, depending on the amount of endochitinase and/or exochitinase present in the sample and on the sensitivity of assay method employed.

The reaction between endochitinase and/or exochitinase and the chitinase substrate of the present invention usually occurs rapidly, and will liberate or produce an intensity of color or fluorescence when the chitinase substrate is a chromogenic or fluorogenic substrate. The intensity of color or fluorescence liberated generally will be visible in less than 30 seconds, and may suitably take place over a period of from about 5 seconds to about 30 minutes.

Examples of suitable fluorogenic substrates (or fluorophores) for exochitinase include, but are not limited to, the certain following derivatives of N-acetyl-β-D-glucosamine (NAG) having a group (or groups) from the following compounds attached to NAG: 1) hydroxy-substituted coumarins, such as 7-hydroxycoumarin (also referred to as umbelliferone) and 7-hydroxy-4-methylcoumarin (also referred to as 4-methylumbelliferone or 4MU), 4-trifluoromethylumbelliferone, 6,8-difluoro-4-methylumbelliferone, 3-cyanoumbelliferone and 3-carboxyumbelliferone; 2) amino-substituted coumarins, such as 7-amino-4-methylcoumarin and 7-amino-4-trifluoromethylcuomarin; 3) aminoquinoline and its derivatives; 4) fluorescein, 5-aminofluorescein and their derivatives; 5) fluorescamine and its derivatives; 6) rhodamine and its derivatives; 7) resorufin and its derivatives; 8) dimethylacridinone and its derivatives; 9) BODIPY FL and-its derivatives; 10) naphthalene and its derivatives; 11) dansyl chloride and its derivatives; 12) eosin 5-isothiocyanate, eosin B, eosin Y and their derivatives; 13) 4',6-diamidino-2-phenylindole (also referred to as DAPI); 14) o-phthaldehyde; 15) erythrosine B; 16) 4-acetamido-4'-isothiocyanatostilbene-2-2'-disulfonic acid; 17) 4-4'-diisothiocyanatostilbene-2-2'-disulfonic acid; 18) 4-(dimethylamino)azobenzene-2,2'-sulfonyl chloride; and 19) other fluorophores. Fluorogenic substrates for endochitinase include the above-mentioned fluorescent dyes that are attached to at least two consecutive NAG residues (such as NAG dimers, trimers, tetramers or oligomers). Example of this group of substrates for exochitinase and endochitinase include 4-methylumbelliferyl-N-acetyl-β-D-glucosaminide (also referred to as 4MU-NAG), 4-methyumbelliferyl-β-D-N,N'-diacetylchitobioside (also referred to as 4MU-(NAG)$_2$, 4-methylumbelliferyl-β-D-N,N',N''-triacetylchitotrioside (also referred to as 4MU-(NAG)$_3$), and 4-methylumbelliferyl-β-D-N,N,N'',N'''-tetraacetylchitotetraoside (also referred to as 4MU-(NAG)$_4$).

Examples of suitable chromogenic substrates (or chromophores) for exochitinase include, but are not limited to, the certain following derivatives of N-acetyl-β-D-glucosamine (NAG) having a group (or groups) from the following compounds attached to NAG: 1) 2-nitrophenol (also referred to as o-nitrophenol); 2) 4-nitrophenol (also referred to as p-nitrophenol); and 3) indolyl chromophores derived from 3-hydroxy indole, 5-bromo-4-chloro-3-indole, 5-bromo-6-chloro-3-indole, 6-chloro-3-indole, 5-iodo-3-indole and N-methyl-3-indole. Chromogenic substrates for endochitinase include the above-mentioned colored compounds that are attached to at least two consecutive NAG residues (such as NAG dimers, trimers, tetramers or oligomers). Examples of this group of substrates for exochitinase and endochitinase include p-nitrophenyl-N-acetyl-β-D-glucosaminide (also referred to as pNP-NAG), p-nitrophenyl-β-D-N,N'-diacetylchitobioside (also referred to as pNP-(NAG)$_2$), p-nitrophenyl-β-D-N,N',N''-triacetylchitotrioside (also referred to as pNP-(NAG)$_3$), and p-nitrophenyl-β-D-N,N',N'',N'''-tetraacetylchitotetraoside (also referred to as pNP(NAG)$_4$).

Then, the presence of allergens and/or total allergen level in the sample, and/or environment, is determined or assessed by detecting, observing and/or measuring the change in color or fluorescence, or the intensity liberated thereof, following contact of the sample with the substrate composition. The intensity of color or fluorescence liberated is proportional to the total allergen level in the sample, which can then be used to estimate the total allergen level in the environment.

The intensity of color liberated following contact of the sample with the substrate composition may be visually observed or detected by any color detecting tool, device, instrument or system known in the art. The intensity of fluorescence liberated can be detected by a fluorometer, a handheld ultraviolet (UV) light or any other fluorescence excitation and/or detecting tool, device, instrument or system known in the art.

Alternatively or in addition, the intensity of color or fluorescence liberated following contact of the sample with the substrate composition is measured or is compared with a reference standard, such as a reference chart, reference paper indicator strip, and the like, having correlation between the intensity of color or fluorescence liberated after a fixed period of time and the total allergen level. The liberated intensity of color or fluorescence can be measured with any fluorescence or color measuring tool, device, instrument or system known in the art, such as a Turner fluorometer.

In accordance with a further aspect of the invention, there is provided a method for decreasing or eliminating the incidence of allergic reactions or asthma. This method comprises the allergen detection and/or determination procedures, in accordance with the method described above, then, removing the materials containing the allergens, and/or the allergens themselves, from the area where unacceptable allergen levels are detected. The efficiency of the allergen removal process can also be monitored by the allergen testing procedure described above.

In the embodiments described herein, the method may further comprise sieving the sample prior to contacting the sample with the substrate composition. In addition, the step of contacting the sample and the substrate composition may include extracting the sample with a buffer solution to produce an extract comprising the chitinases, then contacting the extract and a buffer solution comprising the substrate composition for a brief period of time, then by terminating the reaction. This additional step is particularly useful if the substrate composition is a solid, such as a porous material impregnated with a chitinase substrate. For purposes of testing in accordance with the present invention, the buffer solution used in extracting a sample is suitably of a volume of about 0.1 ml to about 5 ml, and suitably is a phosphate buffer solution having a concentration of about 5 mM to about 100 mM and/or a pH of about 6.0 to about 8.0. In general, the chitinases (exochitinase and endochitinase) are very stable and any buffer that does not inactivate them can be used and this includes acetate buffer (pH 4.0 to 6.0) and Tris buffer (pH 7.0 to 9.0). The buffer solution used in generating the extract is suitably of a volume of about 0.03 ml to about 3 ml. The temperature of the extract contacting step is suitably at about room temperature. Termination of the reaction is suitably done by adding a volume of about 0.5 M to about 2.0 M glycine.

In accordance with the test kit of the invention, the test kit comprises a substrate composition comprising a chitinase substrate and a reference standard. The substrate composition is as described in connection with the method aspect of this intention, and is suitable for contacting a sample of the invention to liberate an intensity of color or fluorescence following contact of the sample with the substrate composition. The reference standard is as described in connection with the method aspect of this intention, and provides a correlation between the intensity of color or fluorescence liberated after a fixed period of contact time and the total allergen level in the sample.

The test kit may also comprise means for sieving a sample to separate out debris and undegraded body components such as intact body parts prior to testing of the sample. The test kit may further comprise means for performing the extraction steps as described in connection with the method aspect of this intention. The test kit may further include means for measuring the amount of the sample and delivering a measured amount of substrate composition comprising chitinase substrate for contact with the sample.

The following examples demonstrate the use of the present invention. A cockroach colony was maintained in a laboratory from 1995 to present. 4 different frass samples were collected during July 1998 and June 2000.

EXAMPLE 1

Detection of Endochitinase and Exochitinase from Cockroach Frass Samples

A cockroach colony was maintained in a 120 gallon rectangular container with about 100,000 Germ an cockroaches. Eastern white pine wood shavings were placed at the bottom of the container where the cockroaches were. Pine wood boards were then staked on top of one other with ¼ inch thick spacers between them to allow 10 cockroach to nest between each set of boards. Dishes of food (laboratory chow) and water were placed on top of the pine wood boards. The containers were covered with cloth liners to prevent the escape of cockroaches.

Different frass samples of about 1.0 gram containing decayed dried dead body parts, fecal pellets, cuticles and egg cases, and secretions were collected from the bottom of the maintained cockroach colony. Frass extracts were prepared by homogenizing each frass sample in 5 ml of phosphate-buffered saline solution (PBS) at pH 7.4 followed by centrifugation at 13,000 g for 30 minutes. Each supernatant sample was dialyzed overnight first against the same buffer then against deionized water to remove the low molecular weight impurities. The frass proteins in each frass extract were separated by polyacrylamide gel electrophoresis in the presence of sodium dodecyl sulfate (SDS-PAGE) at a constant voltage of 200 V at room temperature. After renaturation of the separated proteins with 2.5% Triton X-100, which is a non-ionic detergent that is used for removing SDS, for 30 min. with gentle agitation, the gel was probed with the fluorogenic substrates by a process called fluorimetric zymography. When the gel was probed with 0.25 mM 4MU-$(NAG)_3$, it was found that the frass extract from the frass sample collected in June 1999 contained a very strong endochitinase activity with a molecular weight ($M_r$) of approximately 25,000 (FIG. 1, lane 1). We have also found that both 4MU-$(NAG)_4$ and 4MU-$(NAG)_2$ were hydrolyzed by endochitinase (results not shown). When 0.25 mM 4MU-NAG was used, an exochitinase activity with a $M_r$ of approximately 85,000 was detected (FIG. 1, lane 2). All 4 extracts showed very similar endochitinase and exochitinase activities or profiles.

EXAMPLE 2

The Stabilities of Endochitinase and Exochitinase to Heating and pHs

Cockroach allergens are known to be exceptionally stable. The stabilities of both endochitinase and exochitinase were determined at 100° C. and at different pHs. The June 1999 frass extract, as derived in EXAMPLE 1, containing both exochitinase and endochitinase was heated at 100° C. for 20 min. Either 4MU-$(NAG)_3$ (for endochitinase) or 4MU-NAG (for exochitinase) substrate was added (final concentration of substrate was 1 µM) to react with the enzymes in the heated extract. The liberated fluorescence was measured using a Turner fluorometer with an excitation wavelength of 360 nm and an emission wavelength of 450 nm. A reading of one equals one activity unit. It was found that both heated enzymes retained full activity at 100° C. when compared to the unheated samples (results not shown). The stabilities of endochitinase and exochitinase were also determined at a pH range of 4.0 to 9.0. The extract retained full enzymatic activity for both endochitinase and exochitinase at all pH values tested (results not shown). Both endochitinase and exochitinase were also found to be stable at room temperature for at least 5 years (results not shown).

EXAMPLE 3

Correlation of Endochitinase Activity with Total Allergen Level of Different Dust Samples Dust samples of about 0.5 gram were collected from five different apartments and sieved with a 250 micron screen. Each of the sieved samples was extracted with 3 ml of 20 mM phosphate buffer (pH 7.0). Each extract containing the endochitinase was assayed in a final volume of 100 µl of 20 mM phosphate buffer (pH 7.0) containing 1 µM of 4MU-$(NAG)_3$ substrate. After incubating at room temperature for 5 min., each of the reactions was stopped by adding 1 ml of 1.5 M glycine. The liberated fluorescence was measured using a Turner fluorometer as described in EXAMPLE 2. A control sample without the dust extract was also prepared. The reading from this control sample was minimal and was subtracted from the sample reading.

(a) Measurement of Total Allergens

The total allergen levels of the different dust samples were determined by directly spotting the extracts onto a nitrocellulose membrane. The membrane was then immersed in a blocking solution containing 5% non-fat dry milk in Tris-HCl, pH 7.5, 500 mM NaCl, and 0.05% Tween 20 (TTBS) for 2 hrs. The membrane was washed with the same TTBS buffer and immunoprobed with a primary antibody solution overnight. This primary antibody was obtained from pooled sera collected from individuals that were known to have asthmatic symptoms caused by German cockroaches. The blot was washed and then incubated for 2 hrs. with an alkaline phosphatase-tagged secondary antibody solution (anti-human IgE). The allergens were detected by staining with 5-bromo-4-chloro-3-indolyl phosphate/nitro blue tetrazolium (BCIP/NBT). The intensity of the color generated by the total allergens was determined via an ImageQuant program (Molecular Dynamics Corp). As shown in Table 1, the endochitinase activity of each dust sample is proportional to the total allergen level of that respective dust sample. Essentially identical results were also obtained when the tag on the secondary antibody was peroxidase instead of alkaline phosphatase. The colored substrate for peroxidase was 4-chloro-1-naphthol.

EXAMPLE 4

Correlation of Exochitinase Activity with Total Allergen Level of Different Dust Samples Dust samples were collected from five different apartments and sieved as described in EXAMPLE 3. The methods for determining the exochitinase activity was the same as described in EXAMPLE 3, except that 4MU-NAG instead of 4MU-$(NAG)_3$ was used as the substrate. The total allergen level of each dust sample was determined as described in EXAMPLE 3(a). The results in Table 1 indicate that there is a correlation between exochitinase activity of each dust sample and the total allergen level of that dust sample. The proportionality of the exochitinase activity to the endochitinase activity suggest that these two enzymes are closely associated with and possibly form complexes with one another.

EXAMPLE 5

Correlation of Endochitinase Activity with Total Allergen Level of Different Frass Samples Four different frass samples of about 1.0 gram containing decayed dried body parts, decayed fecal pellets, decayed shed cuticles and egg cases, and secretions were collected from the bottom of the maintained cockroach colony as described in EXAMPLE 1. Extracts of the frass samples were then prepared as described in EXAMPLE 1. The endochitinase activity and total allergen level of each frass extract were determined as described in EXAMPLE 3. As shown in Table 1, a correlation can be established between the endochitinase activity and the total allergen level of each different frass sample. Endochitinase activity was found to be present in all four frass components (decayed fecal pellets, decayed dried body parts, decayed shed cuticles and egg cases, and secretions) (results not shown). The endochitinase activity of live cockroaches (whole body extract) was also tested. Only low level of the enzyme was detected (results not shown).

EXAMPLE 6

Correlation of Exochitinase Activity with Total Allergen Level of Different Frass Samples Four different frass samples of about 1.0 gram were prepared as described in EXAMPLE 5. The methods for determining the exochitinase activity and total allergen level were the same as those described in EXAMPLE 3, except that 4MU-NAG instead of 4MU-$(NAG)_3$ was used as the substrate. The results in Table 1 indicate that there is a correlation between exochitinase activity and the total allergen level of each frass sample. Exochitinase activity was found to be present in all four frass components (results not shown). The exochitinase activity of live cockroaches (whole body extract) was also tested. Only low level of the enzyme was detected (results not shown).

The results obtained from EXAMPLES 3 to 6 were plotted as a graph and shown in FIG. 2. It is evident that the endochitinase activity or exochitinase activity of each respective frass sample or dust sample is proportional to the total allergen level of that respective frass sample or dust sample. Thus, the allergens from the collected dust samples can be established to have originated from frass components. Consequently, determination of the level of either one of these two enzyme markers in a dust sample represents a new method for detecting or quantifying the level of total indoor cockroach allergens.

EXAMPLE 7

Detection Limit for Endochitinase and Exochitinase

Both 4MU-$(NAG)_3$ and 4MU-NAG were used as substrates for endochitinase and exochitinase, respectively, and the liberated 4-methylumbelliferone (4MU) was assayed fluorometrically as indicated in EXAMPLE 3. To determine the limit of detection, a series of diluted 4MU solutions were prepared and their fluorescence measured as described in EXAMPLE 3 (FIG. 3, top panel). 2 µl were taken from each of the 4MU solutions corresponding to 20, 40, 60, 80 and 100 ng of 4MU and spotted directly onto a Whatman No. 1 paper and the fluorescence detected by a handheld UV light (FIG. 3, bottom panel). As little as 20 ng or $5 \times 10^{-8}$M of 4MU was detected. A standard reference chart containing known amounts of 4MU was prepared and used to quantitate the activity of enzymes present in various dust samples or their extracts. Similarly, a standard color reference chart using p-nitrophenol (pNP) was prepared.

EXAMPLE 8

The preferred embodiment for detecting either endochitinase or exochitinase is the use of an enzyme substrate (such as 4MU-$(NAG)_3$ for endochitinase and 4MU-NAG for exochitinase, both at 5 µM), impregnated onto a carrier support. Examples of the carrier supports are filter paper, nitrocellulose, nylon, polyvinylidene difluoride (PVDF) or other types of membranes. The width of the filter paper or membrane was around 0.5 cm but can be variable and the length can be quite long so that when the substrate impregnation was completed, it was rolled into a roll similar to the pH paper marketed by Micro Essential Laboratory, Inc., New York, N.Y. 11210. The substrate-impregnated paper or membrane was then wrapped in an aluminum foil for storage. A short strip of this substrate-impregnated membrane or filter paper was cut out and placed in contact for a period of time from a few seconds to a few minutes with a slightly wetted surface (such as by phosphate buffer, pH 7.0) contaminated with cockroach allergens. The substrates on the filter paper were hydrolyzed by the enzyme (exochitinase or endochitniase depending on the substrates used) soon after contact. After a fixed time period (such as 30 seconds), the intensity of the fluorescence was viewed using the handheld UV light and compared it with a standard reference chart that contained known amounts of 4MU prepared as described in EXAMPLE 7. A control was carried out without the dust sample. Based on the fluorescence intensity from the reference chart, the activity of the enzyme was determined. Since the enzyme activity is proportional to the total allergen level (FIG. 2), the total allergen level was also determined.

Similarly, the chromogenic substrates pNP-$(NAG)_3$ (for endochitinase) and pNP-NAG (for exochitinase) were used. A standard color reference chart containing p-nitrophenol was prepared as described in EXAMPLE 7 and used to determine the total allergen level of the dust samples.

EXAMPLE 9

A modification of the above procedure involves picking up the dust particles by a slightly wet nitrocellulose, nylon or PVDF membrane, scraping off any loosely attached dust particles and allowing the allergens to be bound to the membrane. This was followed by covering the area containing either endochitinase or exochitinase in the allergen sample with a small strip of previously impregnated fluorogenic or chromogenic substrate as described in EXAMPLE 8. The intensity of either the fluorescence or color was then determined by comparing it with the standard reference chart as mentioned in EXAMPLE 8 and the total allergen level was determined also according to EXAMPLE 8.

EXAMPLE 10

As indicated earlier, no methods are currently available that allow direct on-site detection of allergens and/or total allergen level. A simple method for direct determination of the allergen level in indoor areas such as floors, carpets, under kitchen sinks, behind refrigerator, under stove, kitchen bar, kitchen pantry, cabinet over stove, bedroom closets, bathroom, sink under bathroom, and other places frequented by cockroaches in an infested house was developed. An eye-dropper or similar delivery device was used to deliver one drop (or several drops) of either 4MU-$(NAG)_3$, (for endochitinase) or 4MU-NAG (for exochitinase) substrate solution, both at 5 µM, directly onto the surface of the suspected areas followed by observing the liberated fluorescence soon after application using a handheld UV light. After a fixed period of time (such as 30 seconds), the intensity of liberated fluorescence was compared to a standard reference chart and the total allergen level determined as described in EXAMPLE 8. Similarly, the chromogenic substrates (pNP-$(NAG)_3$ for endochitinase and pNP-NAG for exochitinase) were used for determination of the total allergen level.

One of the goals of the present invention is to identify the locations of cockroach nesting places which are usually in cracks and crevices that are very hard to find. In addition to live cockroaches, the nesting places contain their fecal pellets, decayed dried body parts, decayed cuticles and egg cases, and secretions, which are the origin or sources of allergens. The "eye-dropper" method just described had an unexpected usage in that the detection of the locations of allergens and the severity of contamination were determined in a single application. Once the location and severity of allergen contamination were known, the allergen removal process was initiated. Several allergen removal processes such as high pressure steam detergent wash or repeated detergent cleaning were used and found to be moderately effective. The effectiveness of the cleaning process was also monitored by the allergen detection and determination process just described. Allergen removal is essential for the reduction of the incidence of asthma or allergic reaction relating to cockroach allergens.

EXAMPLE 11

Extracts from dust samples were prepared and their allergen levels were determined. Dust samples of about 0.5 gram were collected in small tubes (such as test tubes or Eppendorf tubes). 1 ml of 20 mM phosphate buffer (pH 7.0) was added into each tube and mixed by shaking vigorously several times. After the insoluble materials settled to about the bottom of each tube, the upper level of the solution contained the allergens. A small strip of the substrate-impregnated filter paper or membrane (such as 4MU-$(NAG)_3$ or 4MU-NAG) described in EXAMPLE 8 was dipped into the upper layer containing the allergens. After a fixed period of time (such as 30 seconds), the fluorescence was detected using a handheld UV light and compared it with a standard reference chart. Since the enzyme activity is proportional to the total allergen level (FIG. 2), the total allergen level was then determined. Alternatively, a drop (or several drops) of the upper layer allergen extract was spotted directly onto a membrane or filter paper previously impregnated with the fluorogenic or chromogenic substrates and the liberated fluorescence or color was determined after a fixed period of time (such as 30 seconds).

EXAMPLE 12

A dust sample was collected and extracted as described in EXAMPLE 11. Using an eye-dropper, 1 drop (or several drops) of the top liquid layer was transferred into a test tube (or any clear tube) followed by adding 1 drop of 4MU-NAG substrate, (for exochitinase) or 4MU-$(NAG)_3$ substrate, (for endochitinase), both at 5 µM, into the same tube. After a fixed period of time (such as 30 seconds), the fluorescence of 4MU was then viewed using a handheld UV light and compared it with a standard reference chart.

EXAMPLE 13

Absence of Endochitinase and Exochitinase from Dust Mite Extract

As indicated earlier, aside from cockroach allergens, another source of allergens comes from dust mites in an indoor environment. Even though the preferred locations for these two sources of allergens are different (kitchen and bathroom areas for cockroaches while bedroom and rugs for dust mites), it is of importance to rule out the contribution of exochitinase and endochitinase from dust mites. Dust mite extract was prepared as described in EXAMPLE 1. The endochitinase and exochitinase activities in the dust mite extract and cockroach frass extract were determined by fluorimetric assay described in EXAMPLE 3. The results presented in Table 2 indicated that the dust mite extract did not contain either endochitinase or exochitinase enzymes (or it contained extremely low level of these enzymes). For example, 30 μg of dust mite extract liberated extremely low fluorescence readings when compared with those from the cockroach frass extract which gave very high readings. Therefore, it is concluded that the endochitinase and exochitinase activities from the allergen dust samples originated from cockroaches rather than from dust mites.

Although the examples described above are directed to applications of the present invention in indoor settings or environments, it is obvious to one of ordinary skill in the art that the method and kit of the present invention can also be applicable for use in outdoor and/or semi-outdoor settings where German and/or other types of cockroaches are prevalent. The applicants believe that endochitinase and exochitinase from American and/or other types of cockroaches may behave the same way or similarly to German cockroaches, but the applicants have not carried out such studies. It is known that German cockroaches are primarily found indoor whereas American cockroaches and other types of cockroaches are generally found outdoors.

TABLE 1

Endochitinase and Exochitinase Activity vs. Total Allergen Level For Different Dust and Frass Samples

| Sample | Total Allergen Level (units) | Endochitinase Activity (units) | Exochitinase Activity (units) |
| --- | --- | --- | --- |
| Dust Sample 1 | 40 | 350 | 300 |
| Dust Sample 2 | 56 | 960 | 463 |
| Dust Sample 3 | 126 | 1780 | 910 |
| Dust Sample 4 | 173 | 2612 | 1270 |
| Dust Sample 5 | 187 | 2866 | 1475 |
| Frass Sample 1 | 84 | 1355 | 645 |
| Frass Sample 2 | 107 | 1716 | 830 |
| Frass Sample 3 | 147 | 2356 | 1156 |
| Frass Sample 4 | 208 | 3215 | 1665 |

TABLE 2

Endochitinase and Exochitinase Activity From Dust mite Extracts vs. Cockroach Frass Extracts

| Concentration | Dust mite Extract | | Cockroach Frass Extract | |
| --- | --- | --- | --- | --- |
| | Endochitinase | Exochitinase | Endochitinase | Exochitinase |
| 5 μg | 45 | 49 | 1250 | 590 |
| 10 μg | 51 | 53 | 1730 | 910 |
| 15 μg | 59 | 64 | 2370 | 1403 |
| 20 μg | 75 | 75 | 3189 | 1840 |
| 25 μg | 81 | 85 | 4020 | 2389 |
| 30 μg | 88 | 92 | 4928 | 2829 |

It is to be understood that the present invention is not limited to the preferred or other embodiments described herein, but encompasses all embodiments within the scope of the following claims.

What is claimed is:

1. A method for detecting cockroach allergens in a sample comprising the steps of:
   a) providing a sample from an environment in which cockroaches are present or are suspected to be present;
   b) contacting the sample with a substrate composition comprising a chitinase substrate selected from the group consisting of a fluorogenic substrate, a chromogenic substrate and a mixture thereof, for a period of time under conditions sufficient to cause a change in color or fluorescence when a chitinase is present in the sample; and
   c) detecting the presence of cockroach allergens by correlating the change in color or fluorescence to the presence of cockroach allergens;
   wherein the change in color or fluorescence is proportional to the level of cockroach allergens in the sample.

2. The method according to claim 1, wherein each of the fluorogenic substrate and the chromogenic substrate is a derivative of N-acetyl-β-D-glucosamine.

3. The method according to claim 2, wherein the fluorogenic substrate is selected from the group consisting of 4-methylumbelliferyl-N-acetyl-β-D-glucosaminide, 4-methylumbelliferyl-β-D-N,N'-diacetylchitobioside, 4-methylumbelliferyl-β-D-N,N',N''-triacetylchitotrioside, and 4-methylumbelliferyl-βD-N,N',N'',N'''-tetraacetylchitotetraoside.

4. The method according to claim 2, wherein the chromogenic substrate is selected from the group consisting of p-nitrophenyl-N-acetyl-β-D-glucosaminide, p-nitrophenyl-β-D-N,N'-diacetylchitobioside, p-nitrophenyl-β-D-N,N',N''-triacetylchitotrioside, and p-nitrophenyl-β-D-N,N',N'',N'''-tetraacetylchitotetraoside.

5. The method according to claim 1, wherein the period of contact between the sample and the substrate composition is from about 5 seconds to about 30 minutes.

6. The method according to claim 1, wherein step a) further comprises extracting the sample with a buffer solution to produce an extract, and step b) comprises contacting the extract with the substrate composition for a period of time and terminating the reaction between the extract and the substrate composition.

7. The method according to claim 6, wherein step a) further comprises extracting the sample with a buffer solution to produce an extract, and step b) comprises applying the extract to the chitinase substrate, wherein the chitinase substrate comprises a solid substrate.

8. The method according to claim 1, wherein the sample comprises at least one chitinase selected from the group consisting of endochitinase, exochitinase and chitobiosidase.

9. The method according to claim 1, further comprising step d) removing the allergens from the environment.

10. The method according to claim 9, wherein each of the fluorogenic substrate and the chromogenic substrate is a derivative of N-acetyl-β-D-glucosamine.

11. The method according to claim 10, wherein the fluorogenic substrate is selected from the group consisting of 4-methylumbelliferyl-N-acetyl-β-D-glucosaminide, 4-methylumbelliferyl-β-D-N,N'-diacetylchitobloside, 4-methylumbelliferyl-β-D-N,N',N''-triacetylchitotrioside, and 4-methylumbelliferyl-β-D-N,N',N'',N'''-tetraacetylchitotetraoside.

12. The method according to claim 10, wherein the chromogenic substrate is selected from the group consisting of p-nitrophenyl-N-acetyl-β-D-glucosaminide, p-nitrophenyl-β-D-N,N'-diacetylchitobioside, p-nitrophenyl-β-D-N,N',N''-triacetylchitotrioside, and p-nitrophenyl-β-D-N,N',N'',N'''-tetraacetylchitotetraoside.

13. The method according to claim 9, wherein step a) further comprises extracting the sample with a buffer solution to produce an extract, and step b) comprises contacting the extract with the substrate composition for a sufficient amount of time and terminating the reaction between the extract and the substrate composition.

14. The method according to claim 9, wherein the period of contact between the sample and the substrate composition is from about 5 seconds to about 30 minutes.

15. The method according to claim 9, further comprising monitoring removal of the allergens from the environment.

16. The method according to claim 9, wherein the substrate composition is a solution or suspension.

17. The method according to claim 9, wherein the substrate composition is a solid impregnated with the chitinase substrate.

18. The method according to claim 1, wherein the substrate composition is a solution or suspension.

19. The method according to claim 1, wherein the substrate composition is a solid impregnated with the chitinase substrate.

20. A method for detecting cockroach allergens in a sample comprising the steps of:
   a) obtaining a sample from an environment in which cockroaches are suspected to be present;
   b) extracting the sample with a buffer to form a liquid extract;
   c) contacting the extract with a substrate composition comprising a chitinase substrate, wherein the chitinase substrate is selected from the group consisting of a chromogenic substrate and a fluorescent substrate, for a period of time under conditions sufficient to cause a measurable change in color or fluorescence; and
   d) detecting the presence of cockroach allergens by correlating the change in color or fluorescence to the presence of cockroach allergens;

wherein the change in color or fluorescence is proportional to the level of cockroach allergens in the sample.

21. The method of claim 20 further comprising step e) removing the allergens from the environment.

22. The method of claim 21 further comprising step f) monitoring the removal of allergens from the environment by repeating steps a–d.

* * * * *